(12) United States Patent
Stahl et al.

(10) Patent No.: US 6,679,834 B2
(45) Date of Patent: Jan. 20, 2004

(54) ENDOSCOPIC SUCTION-IRRIGATION INSTRUMENT FOR SURGERY

(75) Inventors: Glenn H. Stahl, Collegeville, PA (US); Mosaddeq Hossain, Somerville, NJ (US); Robert Banik, Long Valley, NJ (US); Li Yue, North Wales, PA (US); Stephen Wilcox, Philadelphia, PA (US)

(73) Assignee: Pilling Weck Incorporated, Hosham, PA (US)

( * ) Notice: Subject to any disclaimer, the term of this patent is extended or adjusted under 35 U.S.C. 154(b) by 0 days.

(21) Appl. No.: 09/955,918

(22) Filed: Sep. 19, 2001

(65) Prior Publication Data

US 2002/0082475 A1 Jun. 27, 2002

Related U.S. Application Data

(60) Provisional application No. 60/234,897, filed on Sep. 22, 2000.

(51) Int. Cl.[7] ............................................. A61B 1/00
(52) U.S. Cl. ..................... 600/131; 600/156; 600/102
(58) Field of Search ............................... 600/156, 158, 600/131, 102

(56) References Cited

U.S. PATENT DOCUMENTS

| | | | |
|---|---|---|---|
| 3,727,605 A | * 4/1973 | Klein | .................. 600/131 |
| 4,400,168 A | 8/1983 | Buechel et al. | |
| 4,998,527 A | * 3/1991 | Meyer | .................. 600/156 |
| 5,016,614 A | * 5/1991 | MacAllister | .............. 600/156 |
| 5,152,278 A | * 10/1992 | Clayman | .................. 600/131 |
| 5,230,704 A | 7/1993 | Moberg et al. | |
| 5,609,573 A | 3/1997 | Sandock | |
| 5,702,349 A | * 12/1997 | Morizumi | .................. 600/131 |
| 5,989,211 A | 11/1999 | Schaumann et al. | |
| 6,413,208 B1 | * 7/2002 | Schollhorn et al. | .......... 600/131 |

OTHER PUBLICATIONS

SLT, 147 Keystone Drive, Montgomeryville, PA 18936, ClearEss, 2 pages.

Medtronic Xomed New Products Spotlight: EndoScrub2, EndoScrub® 2 with Smart–Cycle Software™ your clear advantage, 2 pages.

* cited by examiner

*Primary Examiner*—John Mulcahy
*Assistant Examiner*—Jocelyn Ram
(74) *Attorney, Agent, or Firm*—Howson and Howson

(57) ABSTRACT

An ergonomically superior endoscopic suction-irrigation instrument for surgery comprises a telescope sheath connected at an adjustable angle, preferably approximately 30°, to a vertically elongated handle having thumb-operated irrigation and suction valves and a hook for supporting the handle from the surgeon's hand when the surgeon's grip on the handle is loosened. The instrument is especially suited for sinus surgery.

24 Claims, 9 Drawing Sheets

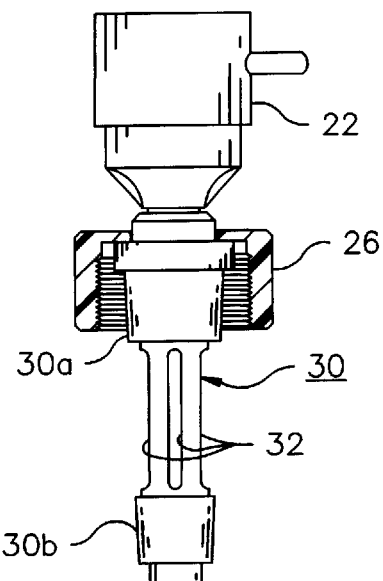
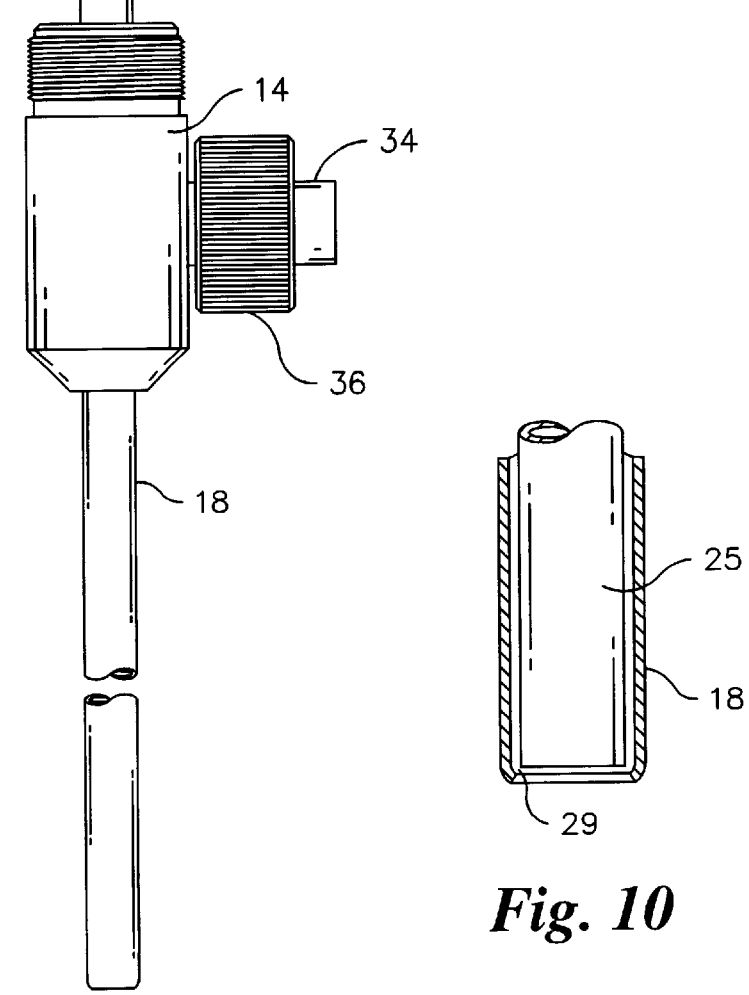
Fig. 9
Fig. 10

US 6,679,834 B2

ENDOSCOPIC SUCTION-IRRIGATION INSTRUMENT FOR SURGERY

CROSS-REFERENCE TO RELATED APPLICATION

This application claims priority based upon provisional application No. 60/234897, filed Sep. 22, 2000.

BACKGROUND OF THE INVENTION

This invention relates generally to surgery and more particularly to improvements in instruments used for suction, irrigation, or both in surgical procedures, for example sinus surgery.

Sinus surgery is typically carried out with the aid of an endoscope. The endoscope is inserted into a patient's nostril to enable the surgeon to observe a magnified view of the surgical field on a monitor connected to a video camera coupled to the endoscope. Nasal/sinus surgery is carried out in a confined, highly vascularized space. Therefore, there is significant splattering of blood and surgical debris onto the endoscope during the surgery. It is important to keep the endoscope lens clear of blood and surgical debris for optimal visualization of the surgical field. Typically, this is accomplished by irrigating the lens of the endoscope or by removing the scope from the nostril for manual cleaning.

The patient is normally under general anesthesia and in a supine position. The telescope is inserted into the nostril and manipulated to position the tip of the scope near the surgical site. The endoscope is typically handled by the surgeon using a finger grip in order to control the position of the endoscope against the forces exerted by the tissue structures and the attachments to the endoscope, such as a video camera head and cables, a fiber optic light carrier and irrigation tubes. This method of handling the endoscope has been found to cause fatigue, especially in longer surgical procedures.

Another problem encountered in conventional endoscopic sinus surgery is encumbered working space. The typical method of gripping the endoscope can limit the working space around the scope for the manipulation of other instruments. This encumbrance is increased when irrigation tubing and/or bulky hand pieces take space around the entrance to the nostril.

Existing pump-driven irrigation systems have foot-operated controls. Locating these controls among other foot-operated equipment, such as the electrosurgical unit and powered cutting devices, is distracting to the surgeon during surgery, since the surgeon must shift his or her position to operate the various controls. These devices are also cumbersome to set up and generally do not provide adequate fluid volume and pressure.

It is an object of this invention to address the aforementioned problems, and it is a general object of this invention to provide an ergonomically superior irrigation system for use in sinus surgery and in other surgical operations where irrigation and/or suction are required.

SUMMARY OF THE INVENTION

A preferred endoscopic instrument in accordance with the invention comprises a tubular sheath extending along a sheath axis, the sheath having an internal passage for receiving a telescope, the internal passage extending from a proximal, telescope-receiving opening to a distal tip, and a port for connection to suction and irrigation lines; a handle having a manually graspable external surface; a suction valve within the handle, the suction valve being connectible to a suction line and openable to provide communication between said port and the suction line; an irrigation valve within the handle, the irrigation valve being connectible to an irrigation line and openable to provide communication between said port and the irrigation line; manually operable controls on the handle for selectably opening the suction and irrigation valves; and a coupling rigidly connecting the handle to the sheath at an intermediate location along the length of the sheath between the proximal opening and the distal tip; wherein the handle is elongated along a handle axis and oblique relative to the sheath. Preferably, the coupling permits adjustment of the angle between the handle and the sheath. The sheath is releasably locked to the coupling, and rotatable, when released, about the sheath axis. The rotatability of the sheath allows for appropriate positioning of an angle or side-viewing telescope.

Other objects, details and advantages of the invention will be apparent from the following detailed description when read in conjunction with the drawings.

BRIEF DESCRIPTION OF THE DRAWINGS

FIG. 9 is an exploded view, partly in section, showing the telescope sheath and telescope sheath receiver;

FIG. 10 is a fragmentary sectional view showing details of the relationship between the interior of the telescope sheath and the tip of the telescope.

DETAILED DESCRIPTION

Figure 1:
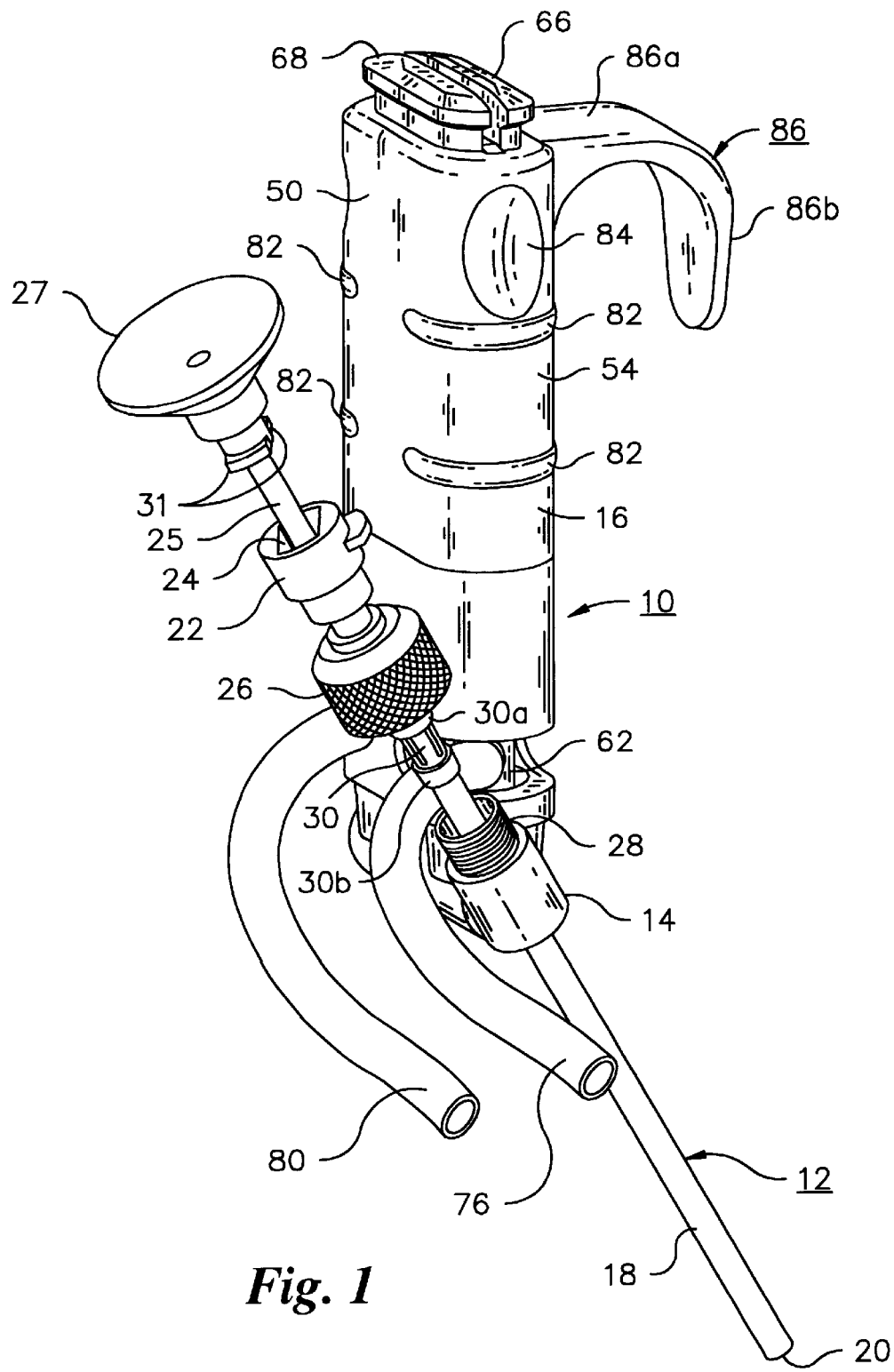
FIG. 1 is an exploded perspective view of an endoscopic instrument in accordance with a preferred embodiment of the invention, showing the telescope and telescope sheath as well as the handle and suction/irrigation valve assembly.
Figure 2:
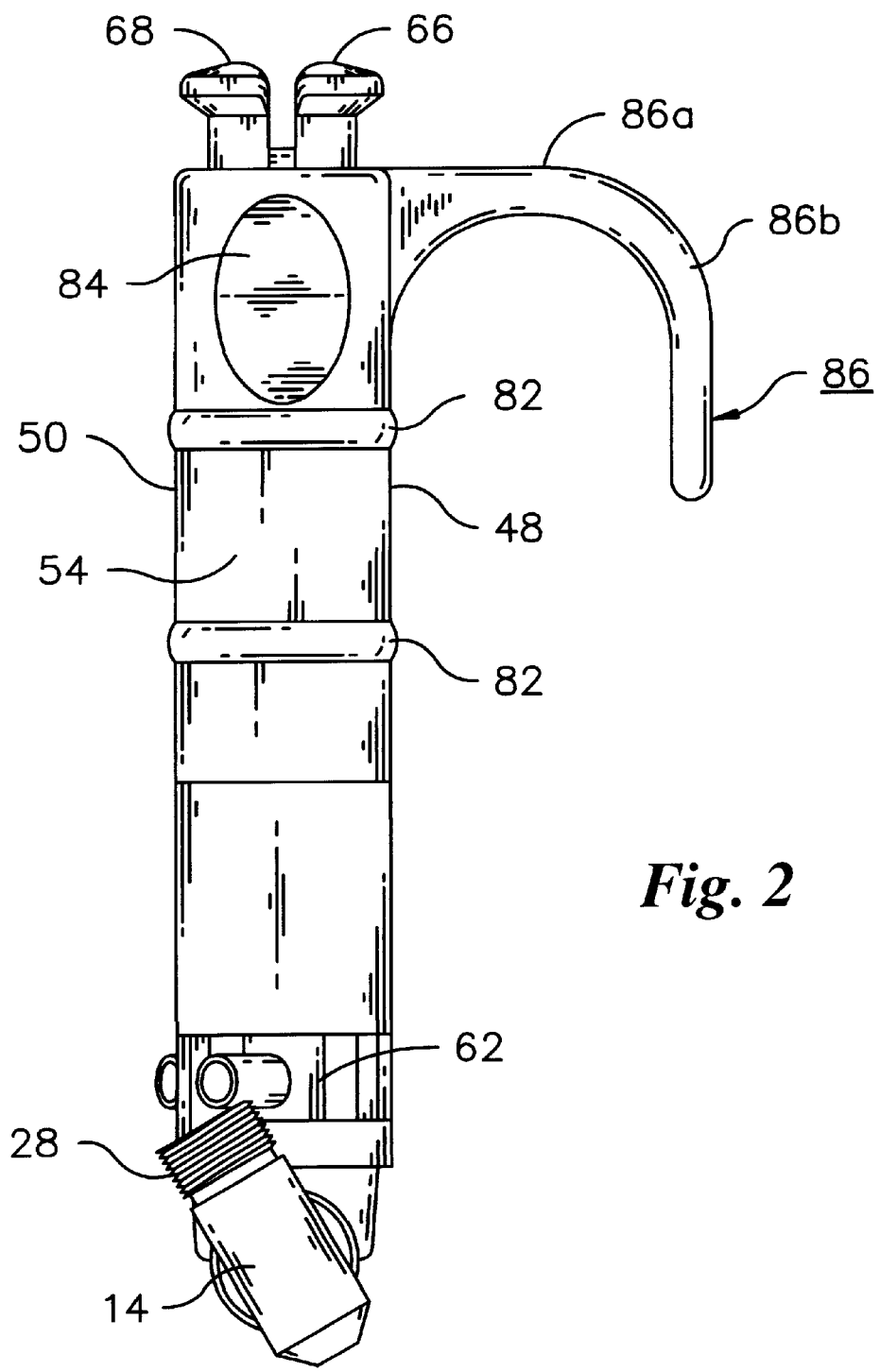
FIG. 2 is a right side elevational view of the handle and valve assembly.

As shown in FIG. 1, the instrument 10 comprises a telescope sheath 12, which is held in a coupling 14 connected to the lower end of an elongated handle 16.

The telescope sheath 12 includes an elongated, hollow tube 18 having an opening at its distal end 20. The sheath has, at its proximal end, a fitting 22 with an opening 24 into which a telescope can be inserted. The telescope used with this instrument typically comprises an eyepiece 27, or alternatively, a miniature television camera (not shown). The eyepiece or camera is connected to the proximal end of a shaft 25, having within it a system of lenses arranged to focus into the eyepiece or television camera a magnified image of the surgical field adjacent the tip of the telescope, which will be at the location of distal end 20 of the tube 18 when the instrument is fully assembled. A fiber optic light carrier is ordinarily provided in the shaft for illuminating the surgical field.

The telescope shaft 25 fits into the sheath 12, extending almost to the opening at the distal end of the tube, as shown in FIG. 10. The inside diameter of the tube 18 is slightly larger than the outside diameter of the telescope shaft 25, providing an annular space for the flow of fluid. An annular clearance 29, between the telescope shaft and the distal end of the tube, allows for the flow of irrigation fluid, usually saline solution, outward from the tip of the tube and for the return of fluid along with blood and debris, drawn into the tube by suction. Since the nasal cavity approximates an oval shape, the exterior of the tube is preferably oval shaped to minimize the interference of the tube with other surgical instruments passed along side the tube inside the nostril. The interior of the tube 18 at its distal end 20 is preferably curved inward to direct irrigation fluid inwardly over the end of the telescope to wash away any accumulated materials that might obstruct the surgeon's view through the telescope or interfere with illumination by the fiber optic light carrier.

The telescope has projections 31, which cooperate with detents (not shown) in opening 24 to lock the telescope in place in the sheath 12. Near the proximal end of sheath 12, just below the fitting 22, is a nut 26, which is rotatable, but restrained against axial movement along the sheath. The nut is engageable with threads 28 on coupling 14, allowing the sheath to be removed for replacement. The sheath can be rotated about its own axis in the coupling 14 and locked by nut 26 in any desired rotational position. Therefore, it is possible to orient a side-viewing telescope locked in the sheath to any desired angle in order to view a field to the side of the telescope axis.

Figure 3:
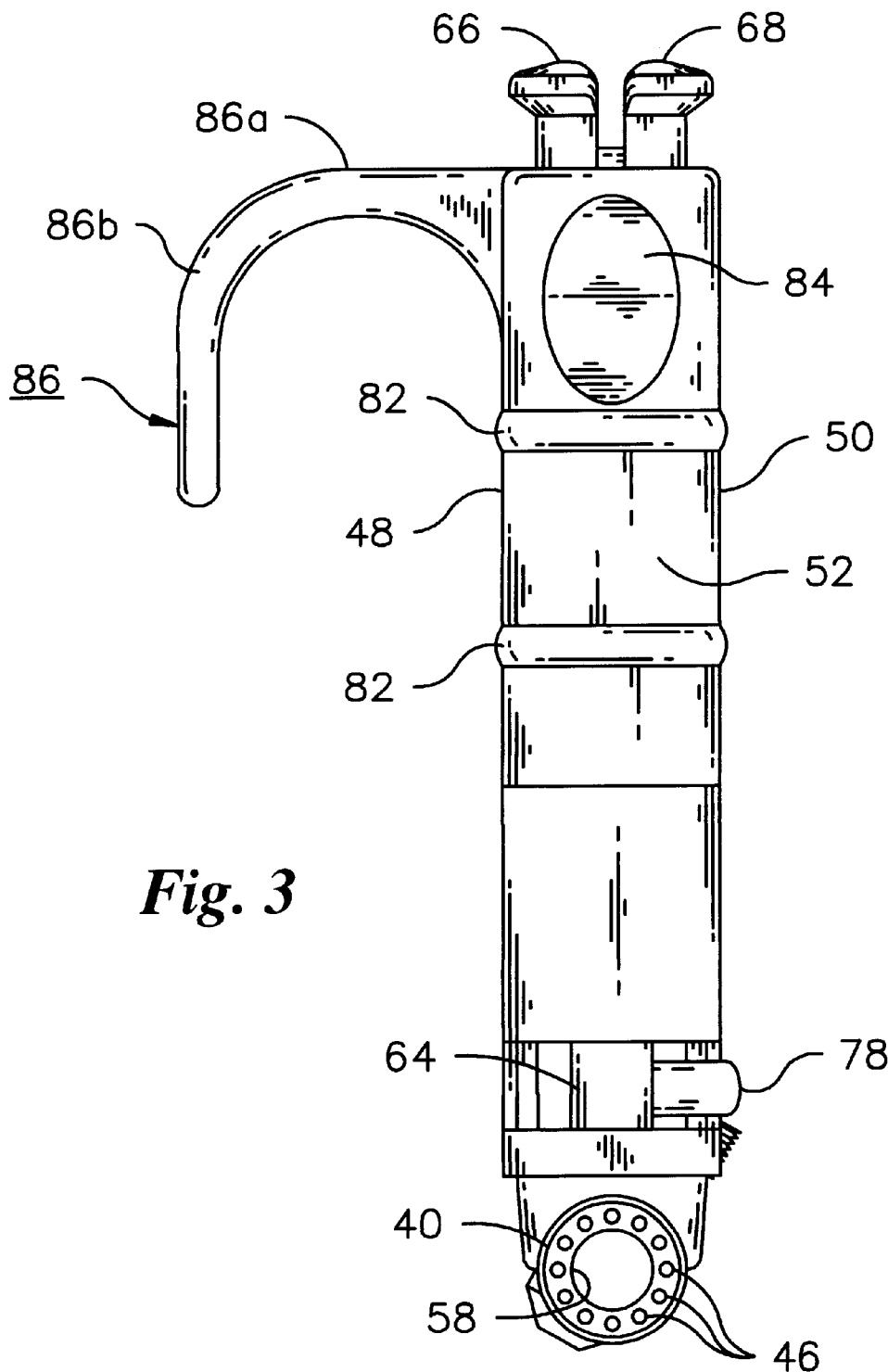
FIG. 3 is a left side elevational view of the handle and valve assembly.
Figure 4:
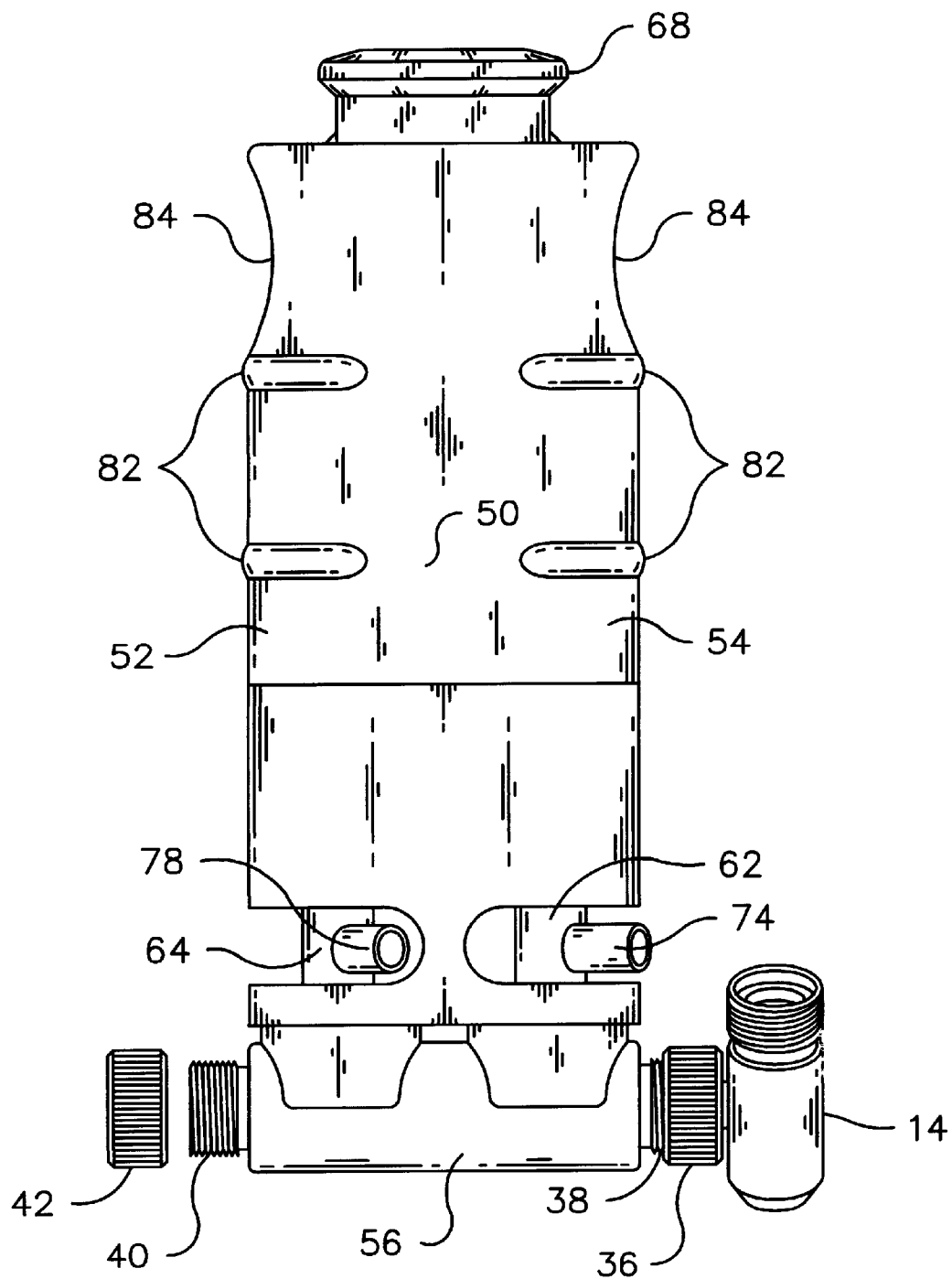
FIG. 4 is a front elevational view of the handle and valve assembly.
Figure 5:
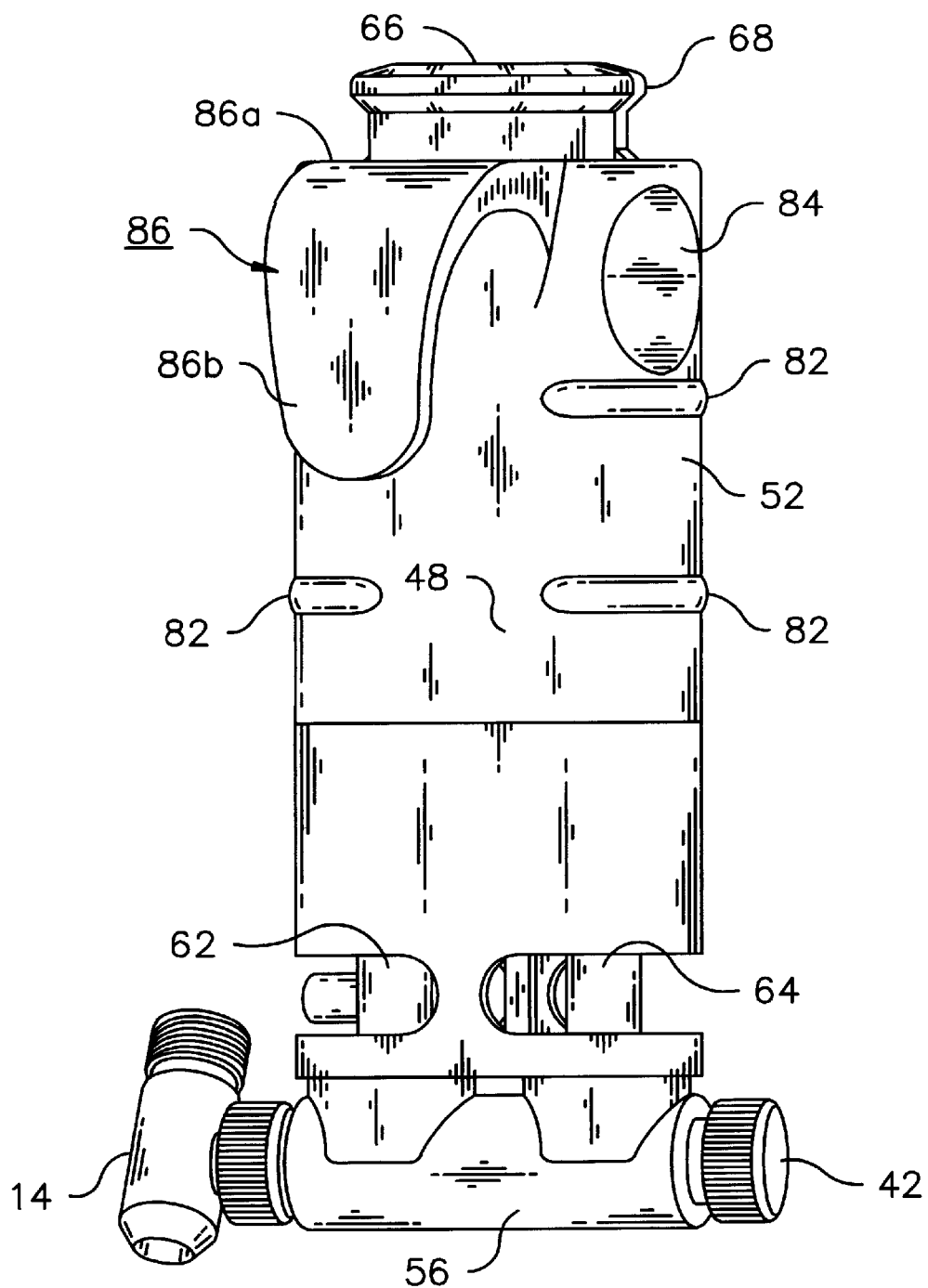
FIG. 5 is a perspective view of the handle and valve assembly.
Figure 8:
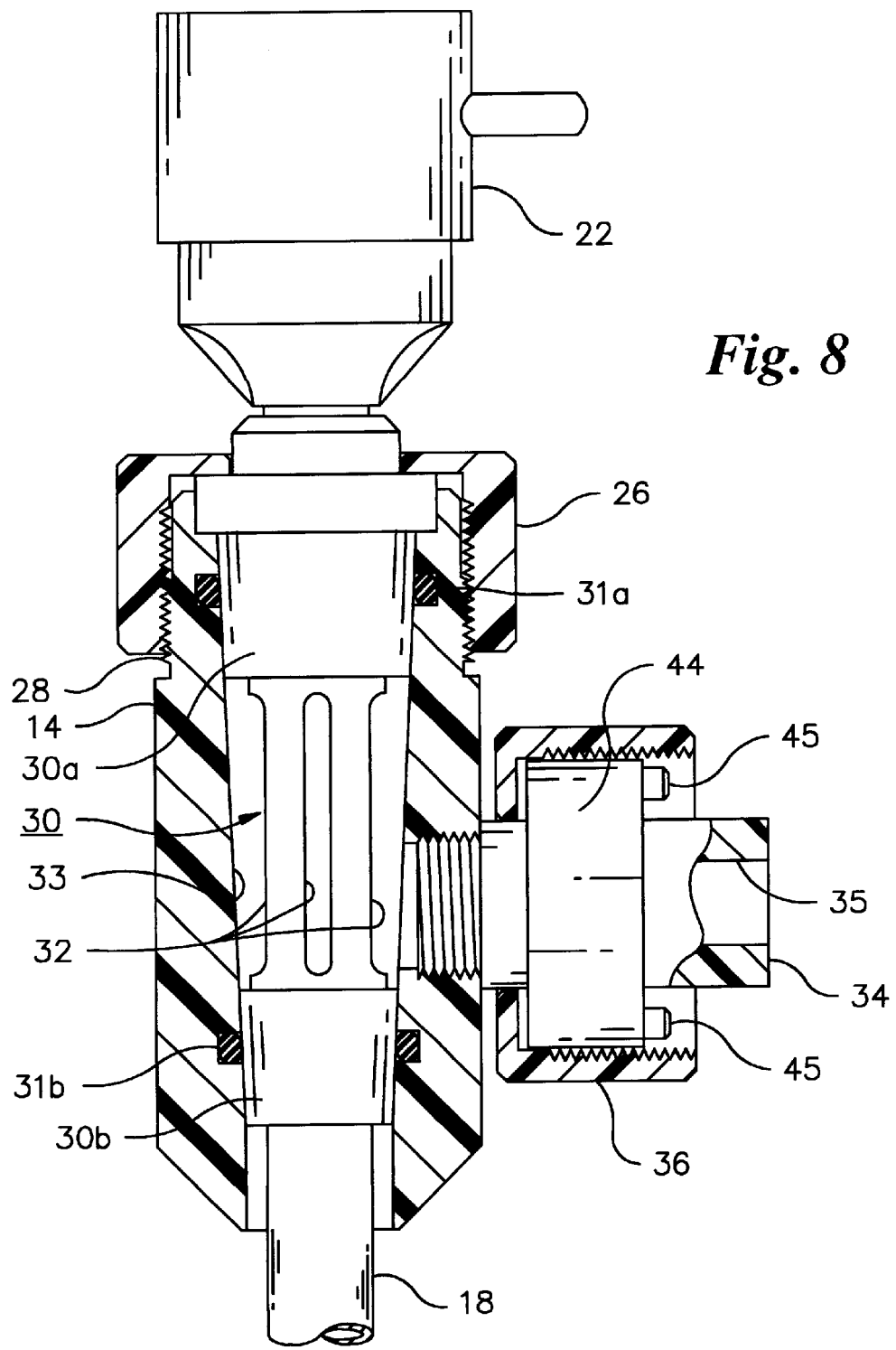
FIG. 8 is a fragmentary sectional view illustrating the fluid connection between the handle and valve assembly and the telescope sheath.

Below the nut, as shown in FIGS. 1, 8 and 9, a tapered element 30, comprising upper and lower, axially spaced, frusto-conical parts 30a and 30b, is provided on the sheath. The tapered element mates in fluid-tight relationship with O-rings 31a and 31b, which serve as seals. The O-rings are located in annular recesses in a tapered hole 33 extending through the coupling 14. Slots 32, which are located on a narrow section of the sheath between parts 30a and 30b, provide fluid communication between the interior of sheath 12 and a fluid channel 35 extending through an adapter 34, which is threaded into a wall of the coupling as shown in FIG. 8 and provided with an internally threaded collar 36, used to secure coupling 14 to a selected one of threaded fittings 38 and 40 the lower end of the handle, as shown in FIG. 4. The unused threaded fitting is closed by a cap 42. As shown in FIG. 8, the adapter 34 is provided with a collar 44, having a pair of projections 45, engageable with a selected opposed pair of depressions formed in an end face of fitting 38. Twelve such depressions 46 are shown in the end face of fitting 40 in FIG. 3. (Fitting 38 has similar depressions.) The engagement of the projections with the depressions allows the coupling to be locked at any selected one of twelve discrete angles with respect to the axis of the handle 16. In this embodiment, the angle of the telescope relative to the longitudinal axis of the handle is limited to twelve discrete angles.

The slots 32 of tapered element 30 are preferably located close to the proximal end of the tube 18 to maximize the length of the portion of tube that can be inserted into the nasal cavity without requiring an excessively long telescope. The fact that the coupling is located to the side of the handle allows the valves to be located within the handle rather than in an assembly aligned with the telescope axis. This, in turn, allows the use of a relatively short coupling, which also contributes to the maximization of the working length of the telescope.

Figure 6:
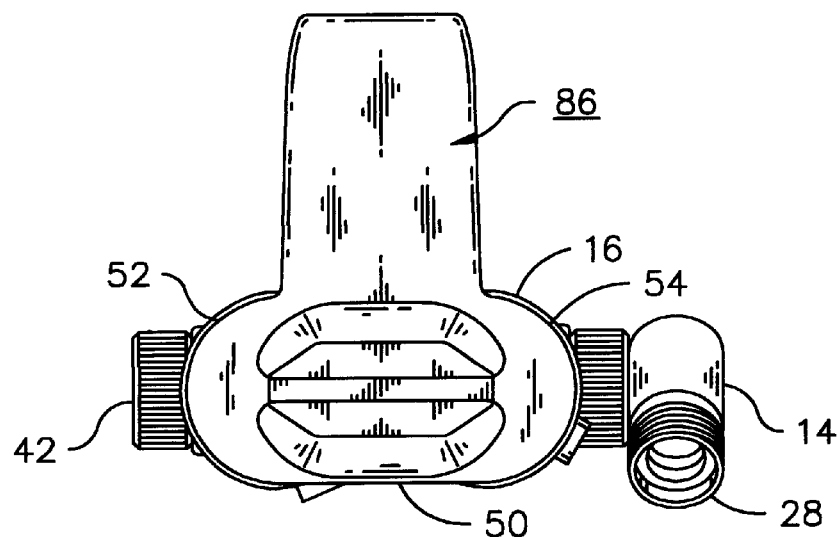
FIG. 6 is a top plan view of the handle and valve assembly.
Figure 7:
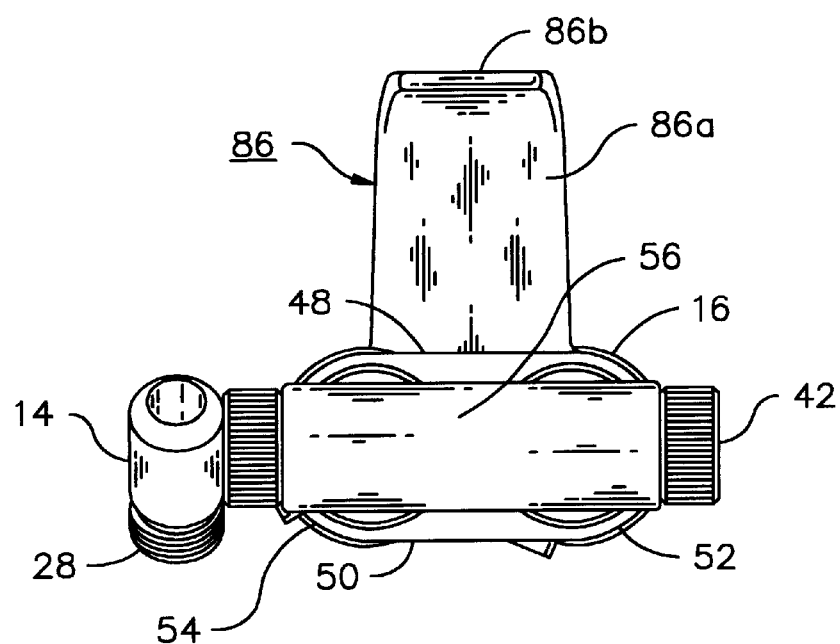
FIG. 7 is a bottom plan view of the handle and valve assembly.

The handle 16 is elongated and, as shown in FIGS. 6 and 7, preferably has a generally oval-shaped, symmetrical, cross-section transverse to its direction of elongation, so that the handle has flat, or nearly flat, wide faces 48 and 50, and arcuate narrow faces 52 and 54. The fittings 38 and 40 extend laterally in perpendicular relation to the axis of elongation of the handle and also perpendicular to the narrow faces of the handle.

Figure 11:
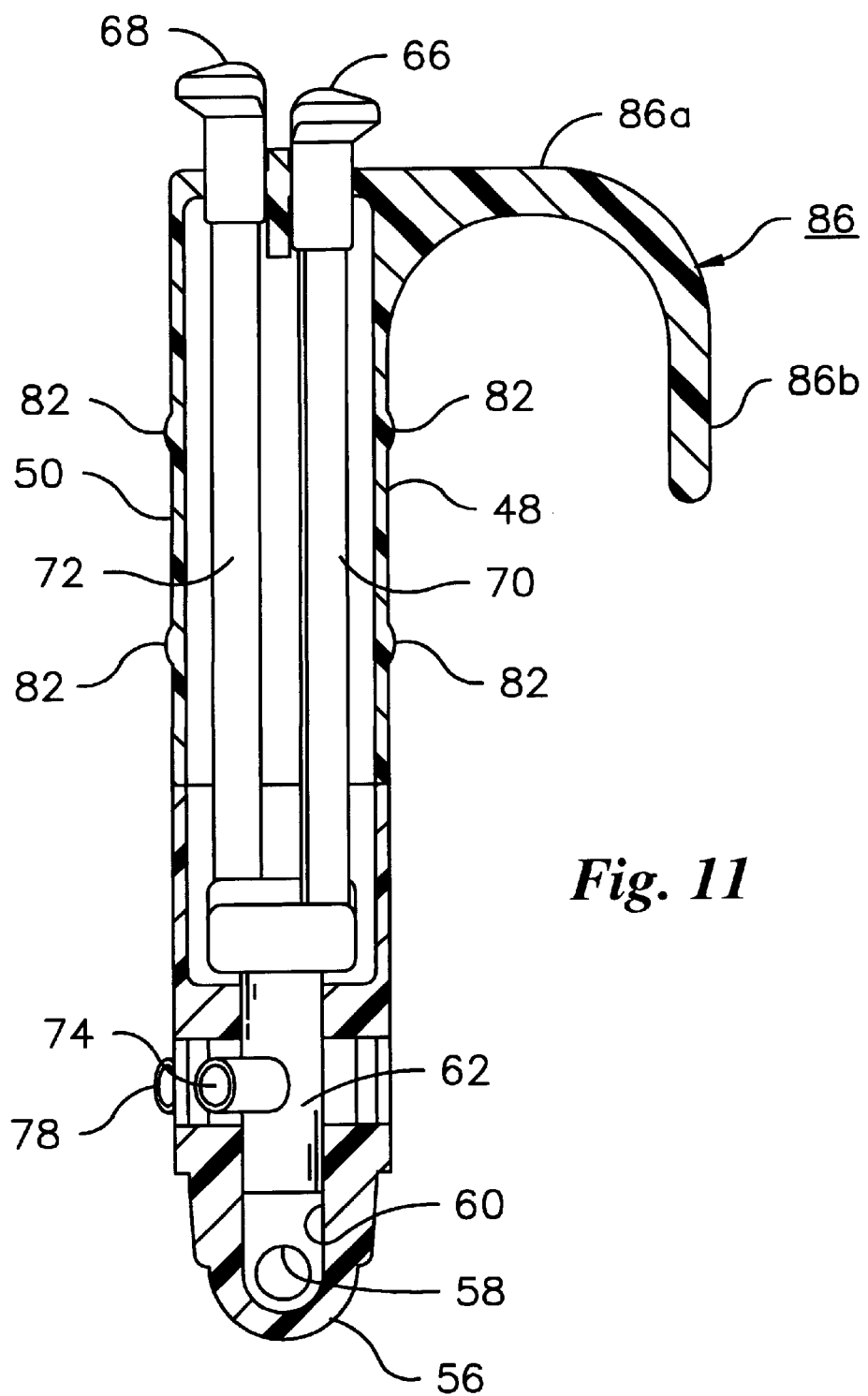
FIG. 11 is a vertical section through the handle, illustrating the operation of the irrigation valve.

As shown in FIG. 11, a manifold 56 is provided at the bottom of the handle. The manifold is provided with two openings, one being opening 58 in fitting 40, the other being a corresponding opening in fitting 38. These openings are of a size to receive, and closely fit, the projecting portion of adapter 34 (FIG. 8), so that the passage 35 in the adapter can communicate with the interior passage 60 of the manifold. The internal passage of the manifold is connected to irrigation and suction ports (not shown) of valves 62 and 64. The valves 62 and 64 are operated respectively by push-buttons 66 and 68 at the top of the handle through internal push-rods 70 and 72. Fitting 74, on valve 62, is connectible to a flexible, tubular irrigation fluid line 76 (FIG. 1), while fitting 78, on valve 64, is connectible to a flexible, tubular suction line 80. The fittings 74 and 78 preferably extend in a direction transverse to a plane defined by the handle axis and the sheath axis so that the suction and irrigation lines extend from the instrument laterally off the operating table rather than toward the head or foot of the patient, and so that the instrument itself can be moved more easily. Optionally, the portions of the valves on which the fittings 74 and 78 are located can be made rotatable about axes parallel to the direction of elongation of the handle so that the suction and irrigation lines can be easily positioned on either side of the operating table.

The exterior surface of the handle preferably has gripping ribs 82 on both short sides and thumb-placement depressions 84 on the short sides near the upper end of the handle.

A hook 86, molded as part of the handle, extends from the upper end of wide face 48 of the handle. As shown in FIGS. 1, 2, 3, 5–7 and 11, the hook comprises a first part 86a extending laterally with respect to the direction of elongation of the handle and a second part 86b extending, from the laterally extending first part, alongside the handle in spaced relation to the handle. The hook is thus designed to rest on the surgeon's hand, normally just above the second metacarpal.

As shown in FIG. 4, because the coupling 14 is selectably attachable to either end of the manifold 56, the instrument can be adapted for use by left or right-handed surgeons. Fluid-tight cap 42 closes the end of the manifold not connected to the coupling.

The ability of the coupling to be locked in any selected one of a plurality of discrete angles relative to the axis of the handle, and the rotatability of the telescope sheath about its own axis make it possible for the surgeon to adjust the irrigation/suction tube to the optimum angle for the surgeon's comfort and for the particular operation being performed. For typical nasal surgery, the coupling 14 will be disposed so that, when the sheath 12 is in the coupling, the axis of the sheath is at an angle of approximately 30 degrees relative to the long axis of the handle. However the angle may vary depending on the position of the patient and the particular surgery being performed. The adjustability of the angle allows the handle to be nearly vertical, i.e. in a neutral position, for optimum comfort to the surgeon. The irrigation and suction buttons 66 and 68 can be easily operated with the thumb without changing the surgeon's grasp on the handle. The hook allows the instrument to rest on the surgeon's hand to minimize fatigue. Moreover, the handle is positioned relative to the tube so that the instrument can be used while the surgeon's arms and/or hands are supported by suitable rests provided on the operating table rails.

The invention has other advantages, including the following. First, by eliminating the need for the surgeon to grasp the instrument, in the conventional manner, along the axis of the telescope, it provides increased space in front of the patient's nostril for the placement and manipulation of other instruments used in sinus surgery. Second, the instrument provides improved irrigation of the distal lens of the telescope, keeping it free of blood and surgical debris, and thereby significantly improving visualization, surgical efficiency and safety. Third, the instrument provides for irrigation of the surgical site for removal of blood and debris from the surgical site itself. Fourth, the instrument is more efficient in that it allows the surgeon to control irrigation by hand rather than by foot control. Fifth, the telescope can be attached to either side of the handle, and therefore the instrument can be used with equal facility by a left-handed or right-handed surgeon. Sixth, the instrument reduces surgeon fatigue because the angle of the telescope relative to the handle can be adjusted, allowing the telescope to be positioned in the patient's nostril at any desired angle, while the handle is held vertically or at another angle most comfortable for the surgeon. Finally, in the case of a side-viewing telescope, the rotatability of the sheath about its own axis also contributes to the reduction of fatigue, by avoiding the need to reposition the handle in order to adjust or change the field of view.

Various modifications can be made to the apparatus described. For example, the coupling can be positioned at the center of the manifold, midway between the narrow faces of the handle and perpendicular to wide face 50. The instrument can, of course, be used in operations other than sinus surgery, and can be modified in various respects depending on its application. Thus other modifications may be made to the apparatus and method described above without departing from the scope of the invention as defined in the following claims.

What is claimed is:

1. An endoscopic instrument for surgery comprising:
   a sheath extending along a sheath axis and having an internal fluid passage;
   a manually graspable handle which is elongated along a handle axis and, when the handle axis is vertical, said handle having upper and lower ends, a pair or wide faces on opposite sides of the handle, and a pair of narrow arcuate faces opposite each other, the handle having an oval-shaped cross-section whereby a width of each of said wide faces is substantially greater than a width of each of said narrow faces; and
   a coupling located adjacent the lower end of the handle, the coupling extending perpendicular to one of said narrow faces, rigidly connecting the handle to the sheath at an intermediate location along the length of the sheath, and holding the sheath with said sheath axis in oblique relationship to the handle axis and in a plane to which said wide faces extend transversely and to which the handle axis is parallel.

2. An endoscopic instrument for surgery according to claim 1, having a projection extending laterally from a location adjacent the upper end of the handle for supporting the instrument by engagement with a portion of a surgeon's hand when the hand is not tightly grasping the handle.

3. An endoscopic instrument for surgery according to claim 2, in which said projection extends laterally from a location adjacent the upper end of the handle in a direction parallel to said plane in which the sheath axis is held.

4. An endoscopic instrument for surgery according to claim 1, in which the angle between the handle axis and the sheath axis is adjustable.

5. An endoscopic instrument for surgery according to claim 4, in which said sheath is rotatable about the sheath axis.

6. An endoscopic instrument for surgery according to claim 4, in which said sheath is releasably locked to said coupling, and rotatable, when released, about the sheath axis.

7. An endoscopic instrument for surgery according to claim 1, having a suction valve within the handle, said suction valve being connectible to a suction line and openable to provide fluid communication between said suction line and said internal fluid passage of the sheath, an irrigation valve within the handle, the irrigation valve being connectible to an irrigation line, and openable to provide fluid communication between said irrigation line and said internal fluid passage of the sheath, and manually operable controls, projecting in the direction of the handle axis, from the upper end of the handle, for selectably opening the suction and irrigation valves.

8. An endoscopic instrument for surgery, comprising:
   a sheath having an internal fluid passage;
   a manually graspable handle which is elongated along a handle axis and having upper and lower ends when the handle axis is vertical;
   a coupling located adjacent the lower end of the handle, the coupling rigidly connecting the handle to the sheath at an intermediate location along the length of the sheath and holding the sheath in oblique relationship to the handle axis; and
   a projection extending laterally from a location adjacent the upper end of the handle for supporting the instrument by engagement with a portion of a surgeon's hand when the hand is not tightly grasping the handle,
   said instrument including a hook, the hook comprising, as a first part thereof, said laterally extending projection, and a second part extending, from the laterally extending projection, alongside the handle in spaced relation to the handle.

9. An endoscopic instrument for surgery, comprising:
   a sheath having an internal fluid passage;
   a manually graspable handle which is elongated along a handle axis and having upper and lower ends when the handle axis is vertical;
   a coupling located adjacent the lower end of the handle, the coupling rigidly connecting the handle to the sheath at an intermediate location along the length of the sheath and holding the sheath in oblique relationship to the handle axis; and
   a projection extending laterally from a location adjacent the upper end of the handle for supporting the instrument by engagement with a portion of a surgeon's hand when the hand is not tightly grasping the handle;
   in which the angle between the handle axis and the sheath is adjustable.

10. An endoscopic instrument for surgery, comprising:
    a sheath having an internal fluid passage;
    a manually graspable handle which is elongated along a handle axis and having upper and lower ends when the handle axis is vertical;

a coupling located adjacent the lower end of the handle, the coupling rigidly connecting the handle to the sheath at an intermediate location along the length of the sheath and holding the sheath in oblique relationship to the handle axis; and a projection extending laterally from a location adjacent the upper end of the handle for supporting the instrument by engagement with a portion of a surgeon's hand when the hand is not tightly grasping the handle;

in which the angle between the handle axis and the sheath is approximately 30 degrees.

11. An endoscopic instrument for surgery, comprising:

a sheath having an internal fluid passage;

a manually graspable handle which is elongated along a handle axis and having upper and lower ends when the handle axis is vertical;

a coupling located adjacent the lower end of the handle, the coupling rigidly connecting the handle to the sheath at an intermediate location along the length of the sheath and holding the sheath in oblique relationship to the handle axis; and a projection extending laterally from a location adjacent the upper end of the handle for supporting the instrument by engagement with a portion of a surgeon's hand when the hand is not tightly grasping the handle;

in which said sheath is removably connected to said coupling by a fluid-tight fitting, and in which said coupling has an internal passage connected to said sheath through said fluid-tight fitting.

12. An endoscopic instrument for surgery, comprising:

a sheath having an internal fluid passage;

a manually graspable handle which is elongated along a handle axis and having upper and lower ends when the handle axis is vertical;

a coupling located adjacent the lower end of the handle, the coupling rigidly connecting the handle to the sheath at an intermediate location along the length of the sheath and holding the sheath in oblique relationship to the handle axis; and a projection extending laterally from a location adjacent the upper end of the handle for supporting the instrument by engagement with a portion of a surgeon's hand when the hand is not tightly grasping the handle;

in which said sheath is removably connected to said coupling by a fitting comprising a pair of axially spaced, frusto-conical, surfaces formed on the exterior of the sheath, and in which said coupling has an internal passage connected to said sheath, and seals mating with said axially spaced, frusto-conical surfaces of the sheath in fluid-tight relationship.

13. An endoscopic instrument for surgery, comprising:

a sheath having an internal fluid passage;

a manually graspable handle which is elongated along a handle axis and having upper and lower ends when the handle axis is vertical; and a coupling located adjacent the lower end of the handle, the coupling rigidly connecting the handle to the sheath at an intermediate location along the length of the sheath and holding the sheath in oblique relationship to the handle axis;

in which the handle is provided, adjacent its lower end, with two fittings respectively on opposite sides of the handle, and in which the coupling is removably connectible to either of said two fittings.

14. An endoscopic instrument for surgery comprising:

a tubular sheath extending along a sheath axis, the sheath having an internal passage for receiving a telescope, the internal passage extending from a proximal, telescope-receiving opening to a distal tip, and a port for connection to suction and irrigation lines;

a handle having a manually graspable external surface and upper and lower ends;

a suction valve within the handle, the suction valve being connectible to a suction line and openable to provide fluid communication between said port and the suction line;

an irrigation valve within the handle, the irrigation valve being connectible to an irrigation line and openable to provide fluid communication between said port and the irrigation line;

manually operable controls for selectably opening the suction and irrigation valves, comprising: a pair of manually depressible buttons located on and projecting upward from the upper end of the handle; and a coupling rigidly connecting the handle to the sheath at an intermediate location along the length of the sheath between the proximal opening and the distal tip;

wherein the handle is elongated along a handle axis which is oblique relative to the sheath axis, the handle axis forms an acute angle relative to the portion of the sheath axis between the proximal opening of the sheath passage and said intermediate location, and said manually operable controls project in the direction of the handle axis, from the upper end of the handle.

15. An endoscopic instrument for surgery, comprising:

a tubular sheath extending along a sheath axis, the sheath having an internal passage for receiving a telescope, the internal passage extending from a proximal, telescope-receiving opening to a distal tip, and a port for connection to suction and irrigation lines;

a handle having a manually graspable external surface;

a suction valve within the handle, the suction valve being connectible to a suction line and openable to provide fluid communication between said port and the suction line;

an irrigation valve within the handle, the irrigation valve being connectible to an irrigation line and openable to provide fluid communication between said port and the irrigation line;

manually operable controls on the handle for selectably opening the suction and irrigation valves; and a coupling rigidly connecting the handle to the sheath at an intermediate location along the length of the sheath between the proximal opening and the distal tip;

wherein the handle is elongated along a handle axis which is oblique relative to the sheath axis, the handle axis forming an acute angle relative to the portion of the sheath axis between the proximal opening of the sheath passage and said intermediate location;

said instrument including a suction fitting on the suction valve, a suction line connected to the suction fitting, an irrigation fitting on the irrigation valve, and an irrigation line connected to the irrigation valve, the suction and irrigation fittings extending in a direction transverse to a plane in which the sheath axis lies, and to which the handle axis is parallel.

16. An endoscopic instrument for surgery, comprising:

a tubular sheath extending along a sheath axis, the sheath having an internal passage for receiving a telescope, the internal passage extending from a proximal, telescope-receiving opening to a distal tip, and a port for connection to suction and irrigation lines;

a handle having a manually graspable external surface;

a suction valve within the handle, the suction valve being connectible to a suction line and openable to provide fluid communication between said port and the suction line;

an irrigation valve within the handle, the irrigation valve being connectible to an irrigation line and openable to provide fluid communication between said port and the irrigation line;

manually operable controls on the handle for selectably opening the suction and irrigation valves; and a coupling rigidly connecting the handle to the sheath at an intermediate location along the length of the sheath between the proximal opening and the distal tip;

wherein the handle is elongated along a handle axis which is oblique relative to the sheath axis, the handle axis forming an acute angle relative to the portion of the sheath axis between the proximal opening of the sheath passage and said intermediate location; and in which the angle between the handle axis and the sheath is adjustable.

17. An endoscopic instrument for surgery according to claim 16, in which the angle between the handle axis and the sheath is selectable from a limited number of discrete angles.

18. An endoscopic instrument for surgery, comprising:

a tubular sheath extending along a sheath axis, the sheath having an internal passage for receiving a telescope, the internal passage extending from a proximal, telescope-receiving opening to a distal tip, and a port for connection to suction and irrigation lines;

a handle having a manually graspable external surface;

a suction valve within the handle, the suction valve being connectible to a suction line and openable to provide fluid communication between said port and the suction line;

an irrigation valve within the handle, the irrigation valve being connectible to an irrigation line and openable to provide fluid communication between said port and the irrigation line;

manually operable controls on the handle for selectably opening the suction and irrigation valves; and a coupling rigidly connecting the handle to the sheath at an intermediate location along the length of the sheath between the proximal opening and the distal tip;

wherein the handle is elongated along a handle axis which is oblique relative to the sheath axis, the handle axis forming an acute angle relative to the portion of the sheath axis between the proximal opening of the sheath passage and said intermediate location; and in which the angle between the handle axis and the sheath axis is approximately 30 degrees.

19. An endoscopic instrument for surgery, comprising:

a tubular sheath extending along a sheath axis, the sheath having an internal passage for receiving a telescope, the internal passage extending from a proximal, telescope-receiving opening to a distal tip, and a port for connection to suction and irrigation lines;

a handle having a manually graspable external surface;

a suction valve within the handle, the suction valve being connectible to a suction line and openable to provide fluid communication between said port and the suction line;

an irrigation valve within the handle, the irrigation valve being connectible to an irrigation line and openable to provide fluid communication between said port and the irrigation line;

manually operable controls on the handle for selectably opening the suction and irrigation valves; and a coupling rigidly connecting the handle to the sheath at an intermediate location along the length of the sheath between the proximal opening and the distal tip;

wherein the handle is elongated along a handle axis which is oblique relative to the sheath axis, the handle axis forming an acute angle relative to the portion of the sheath axis between the proximal opening of the sheath passage and said intermediate location; and in which said sheath is removably connected to said coupling by a fluid-tight fitting, in which said port of the sheath is located at an intermediate location between the proximal opening and the distal tip of the internal passage of the sheath, and in which said coupling has an internal passage connected to said port of the sheath through said fluid-tight fitting.

20. An endoscopic instrument for surgery, comprising:

a tubular sheath extending along a sheath axis, the sheath having an internal passage for receiving a telescope, the internal passage extending from a proximal, telescope-receiving opening to a distal tip, and a port for connection to suction and irrigation lines;

a handle having a manually graspable external surface;

a suction valve within the handle, the suction valve being connectible to a suction line and openable to provide fluid communication between said port and the suction line;

an irrigation valve within the handle, the irrigation valve being connectible to an irrigation line and openable to provide fluid communication between said port and the irrigation line;

manually operable controls on the handle for selectably opening the suction and irrigation valves; and a coupling rigidly connecting the handle to the sheath at an intermediate location along the length of the sheath between the proximal opening and the distal tip;

wherein the handle is elongated along a handle axis which is oblique relative to the sheath axis, the handle axis forming an acute angle relative to the portion of the sheath axis between the proximal opening of the sheath passage and said intermediate location; and in which said sheath is removably connected to said coupling by a fitting comprising a pair of axially spaced, frusto-conical, surfaces formed on the exterior of the sheath at an intermediate location between the proximal opening and the distal tip of the internal passage of the sheath, in which said port of the sheath is located between said axially spaced, frusto-conical surfaces, and in which said coupling has an internal passage connected to said port of the sheath, and seals mating with said axially spaced, frusto-conical surfaces in fluid-tight relationship.

21. An endoscopic instrument for surgery, comprising:

a tubular sheath extending along a sheath axis, the sheath having an internal passage for receiving a telescope, the internal passage extending from a proximal, telescope-receiving opening to a distal tip, and a port for connection to suction and irrigation lines;

a handle having a manually graspable external surface;

a suction valve within the handle, the suction valve being connectible to a suction line and openable to provide fluid communication between said port and the suction line;

an irrigation valve within the handle, the irrigation valve being connectible to an irrigation line and openable to provide fluid communication between said port and the irrigation line;

manually operable controls on the handle for selectably opening the suction and irrigation valves; and a coupling rigidly connecting the handle to the sheath at an intermediate location along the length of the sheath between the proximal opening and the distal tip;

wherein the handle is elongated along a handle axis which is oblique relative to the sheath axis, the handle axis forming an acute angle relative to the portion of the sheath axis between the proximal opening of the sheath passage and said intermediate location; and in which said sheath is releasably locked to said coupling, and rotatable, when released, when said sheath axis.

22. An endoscopic instrument for surgery, comprising:

a tubular sheath extending along a sheath axis, the sheath having an internal passage for receiving a telescope, the internal passage extending from a proximal, telescope-receiving opening to a distal tip, and a port for connection to suction and irrigation lines;

a handle having a manually graspable external surface;

a suction valve within the handle, the suction valve being connectible to a suction line and openable to provide fluid communication between said port and the suction line;

an irrigation valve within the handle, the irrigation valve being connectible to an irrigation line and openable to provide fluid communication between said port and the irrigation line;

manually operable controls on the handle for selectably opening the suction and irrigation valves; and a coupling rigidly connecting the handle to the sheath at an intermediate location along the length of the sheath between the proximal opening and the distal tip;

wherein the handle is elongated along a handle axis which is oblique relative to the sheath axis, the handle axis forming an acute angle relative to the portion of the sheath axis between the proximal opening of the sheath passage and said intermediate location; and in which said handle has upper and lower ends, and includes a hook, extending from a location adjacent the upper end of the handle, the hook comprising a first part extending laterally with respect to the direction of elongation of the handle and a second part extending, from the laterally extending first part, alongside the handle in spaced relation to the handle.

23. An endoscopic instrument for surgery, comprising:

an elongated, tubular sheath extending along a sheath axis, the sheath having an internal passage for receiving a telescope, the internal passage extending from a proximal, telescope-receiving opening to a distal tip, and a fluid port at a location nearer to said telescope-receiving opening than to said distal tip, the fluid port providing fluid communication between the internal passage of the sheath and the exterior of the sheath through a wall of the sheath;

a handle having a manually graspable external surface;

a fitting for connecting the handle to the sheath at the location of said fluid port, the fitting having a fluid passage for carrying fluid into and out of the sheath through said fluid port and a making a fluid-tight connection from the fluid passage to the fluid port; and a telescope extending longitudinally within said sheath from said proximal opening to a location adjacent, but short of, the distal tip, the telescope having an outside dimension such that an annular space for fluid flow is provided between the telescope and an inner face of the wall of the sheath;

in which the exterior of the sheath has an oval cross-section.

24. An endoscopic instrument for surgery, comprising:

an elongated, tubular sheath extending along a sheath axis, the sheath having an internal passage for receiving a telescope, the internal passage extending from a proximal, telescope-receiving opening to a distal tip, and a fluid port at a location nearer to said telescope-receiving opening than to said distal tip, the fluid port providing fluid communication between the internal passage of the sheath and the exterior of the sheath through a wall of the sheath;

a handle having a manually graspable external surface;

a fitting for connecting the handle to the sheath at the location of said fluid port, the fitting having a fluid passage for carrying fluid into and out of the sheath through said fluid port and a making a fluid-tight connection from the fluid passage to the fluid port; and a telescope extending longitudinally within said sheath from said proximal opening to a location adjacent, but short of, the distal tip, the telescope having an outside dimension such that an annular space for fluid flow is provided between the telescope and an inner face of the wall of the sheath;

in which the telescope has a lens at a distal end thereof adjacent, but short of, the distal tip of the sheath, and in which the distal tip of the sheath is curved inward to direct irrigation fluid inwardly over the lens of the telescope to wash away accumulated matter.

* * * * *

UNITED STATES PATENT AND TRADEMARK OFFICE
CERTIFICATE OF CORRECTION

PATENT NO.   : 6,679,834 B2
DATED        : January 20, 2004
INVENTOR(S)  : Glenn H. Stahl et al.

It is certified that error appears in the above-identified patent and that said Letters Patent is hereby corrected as shown below:

Column 5,
Line 48, "or" should read -- of --;

Column 11,
Line 16, "when" should read -- about --;

Signed and Sealed this

Twenty-ninth Day of June, 2004

JON W. DUDAS
*Acting Director of the United States Patent and Trademark Office*